United States Patent [19]

Schönberger et al.

[11] Patent Number: 4,508,900

[45] Date of Patent: Apr. 2, 1985

[54] CATIONIC COMPOUNDS OF THE NAPHTHALIMIDE SERIES, PROCESS FOR THEIR PREPARATION AND THEIR USE

[75] Inventors: Norbert Schönberger, Wehrheim; Erich Schinzel, Hofheim am Taunus; Thomas Martini; Günter Rösch, both of Bad Soden am Taunus, all of Fed. Rep. of Germany

[73] Assignee: Hoechst Aktiengesellschaft, Fed. Rep. of Germany

[21] Appl. No.: 417,052

[22] Filed: Sep. 13, 1982

Related U.S. Application Data

[63] Continuation of Ser. No. 203,530, Nov. 3, 1980, abandoned.

[51] Int. Cl.³ .................. C07D 221/14; D06P 1/649; C09B 17/04
[52] U.S. Cl. .................................. 546/99; 8/648; 106/288 Q
[58] Field of Search .................................. 546/99

[56] References Cited

U.S. PATENT DOCUMENTS

| | | | |
|---|---|---|---|
| 3,625,947 | 12/1971 | Noguchi et al. | 546/96 |
| 3,697,525 | 10/1972 | Okada et al. | 546/99 |
| 3,880,859 | 4/1975 | Scheuermann et al. | 546/99 |
| 3,996,362 | 12/1976 | Wade et al. | 546/99 |

FOREIGN PATENT DOCUMENTS 2331307 1/1975 Fed. Rep. of Germany ........ 546/99
2921641 12/1979 Fed. Rep. of Germany .

OTHER PUBLICATIONS

Schoenberger et al., Chem. Abs. 95, 82398j.

*Primary Examiner*—Mark L. Berch
*Attorney, Agent, or Firm*—Connolly and Hutz

[57] ABSTRACT

Cationic compounds of the formula (1)

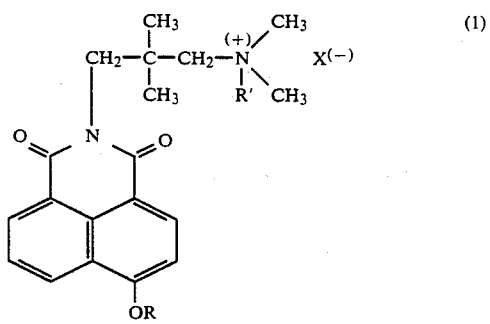

in which
R denotes alkyl, hydroxyalkyl, alkoxyalkyl, phenylalkyl, or phenoxyalkyl,
R' denotes alkyl, hydroxyalkyl, benzyl, or allyl and
$X^{(-)}$ denotes a colorless anion, process for their manufacture and their use.

1 Claim, No Drawings

CATIONIC COMPOUNDS OF THE NAPHTHALIMIDE SERIES, PROCESS FOR THEIR PREPARATION AND THEIR USE

This is a continuation of Ser. No. 203,530 filed Nov. 3, 1980, now abandoned.

Cationic optical brighteners of the naphthalimide series containing quaternary nitrogen atoms are known. French Pat. No. 1,557,945 describes cationic naphthalimide derivatives containing trialkylammonium radicals bound to the imide nitrogen via a chain of two or three methylene groups.

It is the object of the present invention to provide novel cationic compounds of the formula (1)

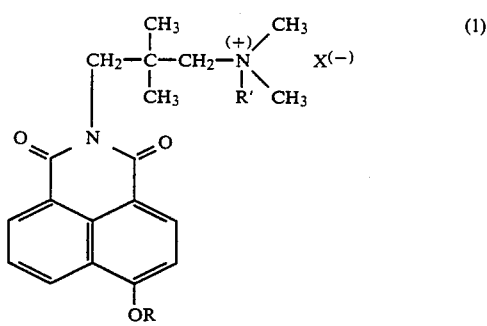

in which

R denotes alkyl, hydroxyalkyl, alkoxyalkyl, phenylalkyl, or phenoxyalkyl,

R' denotes alkyl, hydroxyalkyl, benzyl, or allyl and $X^{(-)}$ denotes a colorless anion.

The radicals R and R' preferably contain 1 to 4 carbon atoms in the alkyl or alkoxy groups and are, for example, ethyl, propyl, butyl, hydroxyethyl, methoxyethyl, ethoxyethyl, propoxyethyl, phenoxyethyl, or benzyl and, in particular, methyl because of the favorable manufacturing conditions. $X^{(-)}$ stands, for example, for a halide, alkyl sulfonate, alkyl sulfate, alkylphenyl sulfonate, or phenyl sulfonate ion.

Compounds of the formula (1) are manufactured in known manner by alkylation of a compound of the formula (2)

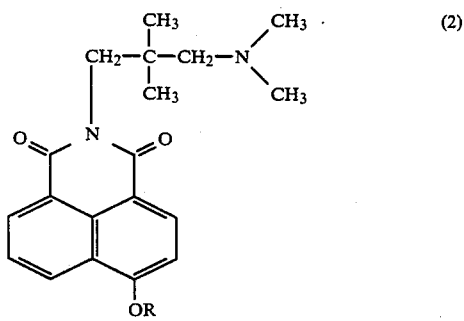

with a compound of the formula

X—R'.

The alkylation is preferably carried out in a suitable inert organic solvent such as toluene, xylene, chlorobenzene, dimethylformamide, or tetraline, at a temperature in the range of from room temperature to 100° C., preferably room temperature to 60° C.

The naphthalimides of the formula (2) used as starting materials are obtained by reaction of the 4-chloro- or 4-bromo-naphthalic anhydrides with N,N,2,2-tetramethylpropane-1,3-diamine(dimethylamino-neopentylamine) to give the corresponding N-(2,2-dimethyl-3-dimethylaminopropyl)-4-halogenonaphthalimides with subsequent exchange of the halogen atoms by reaction with alcohols of the formula HOR or their alkali metal salts.

The novel compounds can be used for brightening organic materials such as cotton and, above all, for synthetic fibers, for example of polyamides such as polymers on the basis of hexamethylene-diamino-adipate or caprolactam, cellulose esters such as cellulose-2½ acetate and cellulose triacetate, and preferably polyacrylonitrile.

For brightening the organic materials a small amount of optical brightener according to the invention, preferably 0.001 to 1%, calculated on the material to be brightened, is incorporated therein, optionally together with other substances such as plasticizers, stabilizers or pigments. The brighteners can be incorporated, into the plastic material, for example, in the form of a solution in a plasticizer, for example dioctyl phthalate, or together with a stabilizer, for example dibutyl tin dilaurate or sodium pentaoctyl tripolyphosphate, or together with pigments, for example titanium dioxide. Depending on the material to be brightened, it is also possible to dissolve the brightener in the monomers prior to polymerization, in the polymer mass, or in a solvent together with the polymer.

The material pretreated in the above manner is then transformed into the desired final shape by processes known per se, such as spinning and drawing. Alternatively, the brightener can be incorporated into finishing agents, for example those for textile fibers, such as polyvinyl alcohol, or into resins or resin precondensates such as methylol compounds of ethylene urea, used for textile treatment.

The compounds of the invention are also suitable to brighten the surface coat of paper. It is preferable, however, to brighten therewith colorless, high molecular weight organic materials in the form of fibers. For brightening said fiber materials it proved advantageous to use an aqueous solution of the compounds of formula (1) according to the invention. The solutions preferably contain from 0.005 to 0.5% of naphthalimides of the invention, calculated on the fiber material. The solutions may further contain auxiliaries such as dispersing agents, for example condensation products of $C_{10}$–$C_{18}$ fatty alcohols or alkylphenols with 15 to 25 moles of ethylene oxide or condensation products of $C_{16}$–$C_{18}$alkyl mono- or polyamines with at least 10 mols of ethylene oxide, organic acids such as formic acid, oxalic acid or acetic acid, detergents, swelling agents such as di- or trichlorobenzenes, wetting agents such as sulfosuccinic acid alkyl esters, bleaching agents such as sodium chlorite, peroxides or hydrosulfites, retarders and optionally other brighteners of the same or another series, for example derivatives of stilbene having an affinity for cellulose.

The fiber material is brightened with the aqueous brightener bath either by an exhaust process at temperatures preferably in the range of from 30° to 150° C. or by a padding process. In the latter case the material is impregnated, for example with a 0.2 to 0.5% brightener solution and finished by a dry or moist heat treatment, for example by steaming under 2 atmospheres or, after drying, by a short dry heating to 180° to 220° C., optionally with simultaneous thermofixation of the fabric. The fiber material treated in this manner is then rinsed and dried.

Colorless, high molecular weight, organic material which has been optically brightened according to the invention, in particular natural or synthetic fiber material that has been brightened by the exhaustion process, has a pleasant, pure white, blue-violet to bluish, fluorescent aspect. When dyed light shades and whitened according to the invention the material is distinguished by a clear shade.

When textile fibers, for example of synthetic polyamide and cellulose ester fibers, in particular polyacrylonitrile fibers, are washed with washing liquors containing a naphthalimide of the formula (1), the material acquires a brilliant aspect in daylight.

It should be stressed that the compounds of the invention have a good stability to light, a high stability to chlorite, a high tinctorial strength and especially a high degree of whiteness and, on the whole, an outstanding tinctorial behavior.

The compounds of the formula (1) containing a quaternary carbon atom in β-position with respect to the quaternary ammonium group and in β-position with respect to the imide nitrogen are extremely stable. They are distinctly superior as regards the brightening effect, especially in the one-bath chlorite bleaching of polyacrylonitrile fibers, to the above mentioned cationic naphthalimides containing trialkylammonium radicals bound to the imide nitrogen via a chain of two or three methylene groups.

The following examples illustrate the invention.

EXAMPLE 1

For preparing the compound

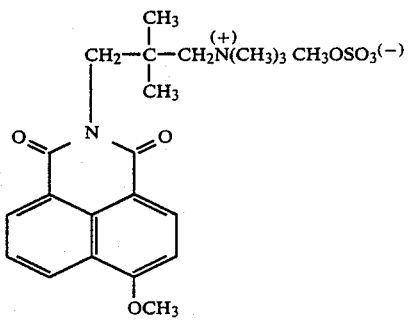

17 g of 4-methoxy-N-dimethylamino-neopentyl-naphthalimide are dissolved in 100 ml of acetone and 5.2 ml of dimethyl sulfate are added dropwise at room temperature. Stirring of the mixture is continued for 18 hours at room temperature, the mixture is filtered with suction and the residue is washed with acetone. After drying in vacuo at 60° C., 21.2 g of a yellowish crystalline powder are obtained, corresponding to 91% of the theoretical. Melting point 231° to 233° C., sintering point 228° C.

The 4-methoxy-N-dimethylamino-neopentyl-naphthalimide required as starting material is prepared as follows: An autoclave with stirrer is charged with 121 g of 4-chloronaphthalic anhydride and 81.4 ml of dimethylamino-neopentylamine in 750 ml of methanol, the autoclave is heated to 70° C. and kept at said temperature for 5 hours. Next, the autoclave is cooled to 50° C., 60 g of 40% sodium hydroxide solution are added and the whole is heated to 100° C. The reaction mixture is stirred for 2 hours at the indicated temperature, cooled to room temperature and the precipitated reaction product is filtered off with suction, washed in portions with 500 ml of methanol and then with water. The precipitate is dried in vacuo at 60° C. 142.0 g of a yellow powder are obtained melting at 107° to 110° C., corresponding to 83.5% of the theoretical.

EXAMPLE 2

0.24 g of sodium chlorite, 0.1 g of a commercial bleaching auxiliary and 0.3 ml of 2N acetic acid are dissolved at 60° C. in 200 ml of water. A solution is prepared from the optical brightener obtained according to Example 1 by dissolving 0.02 g thereof in 1 ml of dimethyl formamide. The solution is added to the aqueous bath and the pH of the bath is adjusted to 3,5 by adding dropwise acetic acid (10% strength). 5 g of a polyacrylonitrile fabric are introduced into the aqueous bath containing the brightener and having a temperature of 60° C. The fabric is first bleached for 30 minutes at 80° C. and then for 30 minutes at 100° C., whereupon it is rinsed with hot and cold water and dried. The fiber material treated in this manner has a pleasant white aspect with a violet hue. A similar effect is obtained by bleaching in the absence of sodium chlorite and bleaching auxiliary and adjusting the pH of the bath to 4 with 10% acetic acid.

EXAMPLE 3

0.12 ml of 85% formic acid is added to 100 ml of water. A solution of the optical brightener according to Example 1 is prepared by dissolving 1 g thereof in 100 ml of water. 1.5 ml of the solution obtained are added to the above solution, the mixture obtained in heated to 60° C. and 3 g of a polyacrylonitrile fabric are introduced. The temperature is raised to 95° to 98° C. within 10 to 15 minutes and the fabric is treated at said temperature for 1 hour. It is then rinsed for 2 minutes in running cold water and dried at 60° C. The treated fabric has a white brilliant aspect.

In the manner described in Example 1 the compounds listed in the following table are prepared

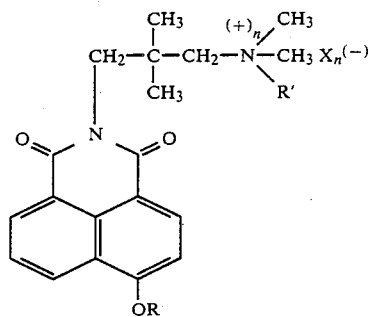

| R | R' | X$^{(-)}$ | n | reaction medium reaction temperature | melting point (purification agent) |
|---|---|---|---|---|---|
| C$_2$H$_5$— | HOCH$_2$CH$_2$— | Cl$^{(-)}$ | 1 | 2-chloroethanol 128° C. | 204.5° C. with decomp. (from pyridine) |
| CH$_3$CH$_2$CH$_2$— | CH$_3$ | CH$_3$OSO$_3^{(-)}$ | | toluene 60° C. | 184–192° C. |
| CH$_3$CH$_2$CH$_2$— | HOCH$_2$CH$_2$— | Cl$^{(-)}$ | | 2-chloroethanol 128° C. | 113–116.5° C. (from ethanol) |
| CH$_3$CH$_2$CH$_2$— | | | | n-propanol 100° C. | 144.5–146.5° C. (from ethanol) |
| CH$_3$— | CH$_3$— | CH$_3$C$_6$H$_5$SO$_3^{(-)}$ | 1 | toluene 60° C. | 222–225° C. |
| CH$_3$— | C$_2$H$_5$— | C$_2$H$_5$SO$_3^{(-)}$ | 1 | diethyl sulfate 50° C. | 198–200° C. (from methanol) |
| CH$_3$— | HOCH$_2$CH$_2$— | Cl$^{(-)}$ | 1 | 2-chloroethanol 128° C. | 218–220° C. with decomp. (from ethanol) |
| CH$_3$— | CH$_3$(CH$_2$)$_3$— | Br$^{(-)}$ | 1 | n-butyl bromide 102° C. | 192–193° C. with decomp. (from isopropanol) |
| C$_2$H$_5$— | CH$_3$— | CH$_3$OSO$_3^{(-)}$ | 1 | toluene 60° C. with decomp. | 233–237° C. (from n-butanol) |
| CH$_3$OCH$_2$CH$_2$— | CH$_3$— | CH$_3$OSO$_3^{(-)}$ | 1 | toluene 60° C. | 220–225° C. |
| C$_2$H$_5$ | | | | ethanol/NaOH 78° C. | 144–146° C. (from cyclohexane) |
| CH$_3$OCH$_2$CH$_2$— | | | | methyl glycol 80° C. | 116–118° C. (from cyclohexane) |

What is claimed is:

1. A cationic compound of the formula:

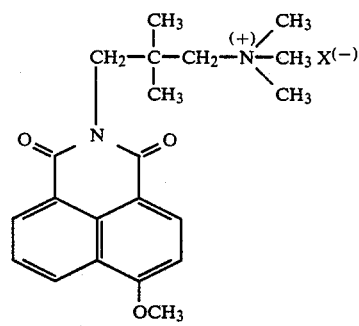

wherein X$^{(-)}$ denotes a colorless anion.

* * * * *